US005932209A

United States Patent [19]
Thompson et al.

[11] Patent Number: 5,932,209
[45] Date of Patent: Aug. 3, 1999

[54] BACILLUS THURINGIENSIS δ-ENDOTOXIN

[75] Inventors: Mark Thompson, Del Mar; George E. Schwab, La Jolla; H. Ernest Schnepf; Brian Stockhoff, both of San Diego, all of Calif.

[73] Assignee: Mycogen Corporation, San Diego, Calif.

[21] Appl. No.: 08/732,495

[22] PCT Filed: May 5, 1995

[86] PCT No.: PCT/US95/05090

§ 371 Date: Mar. 6, 1997

§ 102(e) Date: Mar. 6, 1997

[87] PCT Pub. No.: WO95/30752

PCT Pub. Date: Nov. 16, 1995

Related U.S. Application Data

[63] Continuation-in-part of application No. 08/239,474, May 6, 1994, Pat. No. 5,593,881.

[51] Int. Cl.$^6$ .......................... A01N 63/00; A01N 37/18; C07K 14/325; C12N 1/21
[52] U.S. Cl. ...................... 424/93.2; 435/252.3; 530/350; 530/825; 514/12; 424/93.4; 424/93.461; 424/832
[58] Field of Search ................................ 536/23.4, 23.71; 435/320.1, 252.3, 252.31, 252.33, 254.11; 514/12; 530/350, 825, 93.2; 924/93.4, 93.461, 832

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,695,455 | 9/1987 | Barnes et al. | 424/93.2 |
| 4,797,276 | 1/1989 | Hernstadt et al. | 424/84 |
| 4,849,217 | 7/1989 | Soares et al. | 424/93.461 |
| 4,853,331 | 8/1989 | Hernstadt et al. | 435/252.3 |
| 4,918,006 | 4/1990 | Ellar et al. | 435/69.1 |
| 4,948,734 | 8/1990 | Edwards et al. | 514/2 |
| 5,055,294 | 10/1991 | Gilroy | 424/93.2 |
| 5,128,130 | 7/1992 | Gilroy et al. | 424/93.2 |
| 5,151,363 | 9/1992 | Payne | 435/252.5 |
| 5,208,017 | 5/1993 | Bradfisch et al. | 424/84 |
| 5,593,881 | 1/1997 | Thompson et al. | 435/240.1 |

FOREIGN PATENT DOCUMENTS

95/06730  3/1995  WIPO.

OTHER PUBLICATIONS

Li, J., et al. (1991) "Crystal Structure of Insecticidal δ–Endotoxin from *Bacillus thuringiensis* at 2.5 Å resolution" Nature, vol. 353, pp. 815–821.

Choma, C.T., et al. (1990) "Unusual Proteolysis of the Protoxin and Toxin from *Bacillus thuringiensis* Structural Implications" Eur. J. Biochem. 189:523–527.

Haider, M. Z., et al. "Specificity of *Bacillus thuringiensis* var. *colmeri* insecticidal δ–Endotoxin is determined by differential proteolytic processing of the protoxin by larval gut protease" Eur. J. Biochem. 156:531–540.

Aronson, A. I., et al. (1991) "The Solubility of Inclusion Proteins from *Bacillus thuringiensis* is Dependent upon Protoxin Composition and is a Factor in Toxicity to Insects" Applied and Environmental Microbiology 57(4): 981–986.

Honée, G., et al. (1991) "The C–terminal Domain of the Toxic Fragment of a *Bacillus thuringiensis* Crystal Protein Determines Receptor Binding" Molecular Microbiology 5(11): 2799–2806.

Arvidson, H., et al. (1989) "Specificity of *Bacillus thuringiensis* for Lepidopteran Larvae: Factors involved in vivo and in the Structure of a Purified Toxin." Molecular Microbiology 3(11): 1533–1543.

Honée, G., et al. (1990) "A Translation Fusion Product of Two Different Insecticidal Crystal Protein Genes of *Bacillus thuringiensis* Exhibits an Enlarged Insecticidal Spectrum" Applied and Environmental Microbiology 56(3): 823–825.

Feitelson, J.S., et al. (1992) "*Bacillus thuringiensis*: Insects and Beyond" Biotechnology 10:271–275.

Schnepf, H.E., et al. (1981) "Cloning and Expression of the *Bacillus thuringiensis* Crystal Protein Gene in *Escherichia coli*" Proc. Natl. Acad. Sci. USA 78(5): 2893–2897.

Hofte, H., et al., (1989) "Insecticidal Crystal Proteins of *Bacillus thuringiensis*" Microbiology Reviews 53(2): 242–255.

Kreig, V.A., et al., (1983) "*Bacillus thuringiensis* var. *tenebrionis*, a new pathotype effective against larvae of Coleoptera." Z. Ang. Ent. 96:500–508.

Beegle, C.C. (1978) "Use of Entomogenous Bacteria in Agroecosystems" Developments in Industrial Microbiology 20:97–104.

Couch, T.L. (1980) "Mosquito Pathogenicity of *Bacillus thuringiensis* var *isaelensis*" Developments in Industrial Microbiology 22:61–76.

Gaertner, F.H. (1989) "Cellular Delivery Systems for Insecticidal Proteins: Living and Non–Living Microorganisms" in *Controlled Delivery of Crop Protection Agents*, R.M. Wilkins, ed., Taylor and Francis, New York and London, 1990, pp. 245–255.

Gaertner, F.H., Leo Kim (1988) "Current Applied Recombinant DNA Projects" TIBTECH 6:54–57.

Nakamura et al. Construction of chimeric insecticidal proteins ... Agric. Biol. Chem. 54(3) 715–724, 1990.

Stiekman et al. Recombinant *Bacillus thuringiensis* protein genes and their entomocidal host range. J. Cellular Biochem. 14E: 341, 1990.

Raymond et al. Larvicidal activity of chimeric *bacillus thuringiensis* protoxins. Mol. Microbiol. 4(11):1967–1974, 1990.

*Primary Examiner*—Robert A. Wax
*Assistant Examiner*—Gabriele E. Bugaisky
*Attorney, Agent, or Firm*—Saliwanchik, Lloyd & Saliwanchik

[57] ABSTRACT

An improved *Bacillus thuringiensis* (B.t.) delta-endotoxin is created by the modification of the gene encoding the toxin. The toxicity of a B.t. toxin was improved by replacing the native protoxin segment with an alternate protoxin segment by constructing a chimeric toxin gene.

8 Claims, 7 Drawing Sheets

Fig. 6A

```
                    1
Consensus           MEENNQNQCI PYNCLSNPEE VLLDGERIST GNSSIDISLS LVQFLVSNFV PGGGFLVGLI DFVWGIVGPS QWDAFLVQIE QLINERIAEF
                                                                                                                    90

91                               k          e
Alternate
Consensus           ARNAAIANLE GLGNNFNIYV EAFKEWEEDP NNPATRTRVI DRFRILDGLL ERDIPSFRIS GFEVPLLSVY AQAANLHLAI LRDSVIFGER
                                                                                                                    180

181
Consensus           WGLTTINVNE NYNRLIRHID EYADHCANTY NRGLNNLPKS TYQDWITYNR LRRDLTLTVL DIAAFFPNYD NRRYPIQPVG QLTREVYTDP
                                                                                                                    270

271                                  r
Alternate
Consensus           LINFNPQLQS VAQLPTFNVM ESSAIRNPHL FDILNNLTIF TDWFSVGRNF YWGGHRVISS LIGGGNITSP IYGREANQEP PRSFTFNGPV
                                                                                                                    360

361         i   cqrhh        g                q
Alternate
Consensus           FRTLSNPTLR LLQQPWPAPP FNLRGVEGVE FSTPTNSFTY RGRGTVDSLI ELPPEDNSVP PREGYSHRLC HATFVQRSGT PFLITGVVFS
                                                                                                                    450

451         d
Alternate
Consensus           WTHRSATLTN TIDPERINQI PLVKGFRVWG GTSVITGPGF TGGDILRRNT FGDFVSLQVN INSPITQRYR LRFRYASSRD ARVIVLTGAA
                                                                                                                    540

541                                          e
Consensus           STGVGGQVSV NMPLQKTMEI GENLTSRTFR YTDFSNPFSF RANPDIIGIS EQPLFGAGSI SSGELYIDKI EIILADATFE AESDLERAQK
                                                                                                                    630

631         e   p             q              r              ng          p
Alternate
Alternate
Consensus           AVNALFTSSN QIGLKTDVTD YHIDRVSNLV ECLSDEFCLD EKKELSEKVK HAKRLSDERN LLQDPNFRGI NRQLDRGWRG STDITIQGGD
                                                                                                                    720

721         p       l                e                                   r   fe  s   kcgepnrca
Alternate
Consensus           DVFKENYVTL LGTFDECYPT YLYQKIDESK LKAYTRYQLR GYIEDSQDLE IYLIRYNAKH ETVNVPGTGS LWPLSAPSPI G---------
                                                                                                                    810
```

Fig. 6B

```
            811                              i                e   i         gra                                               900
Alternate   phlewnpdld cscrdge              
Consensus   ---------- ------KCA HHSHHFSLDI DVGCTDLNED LGVWVIFKIK TQDGHARLGN LEFLEEK-PL VGEALARVKR AEKKWRDKRE 901        ql                q                t   r q             g                                              990
Alternate
Consensus   KLEWETNIVY KEAKESVDAL FVNSQYDRLQ ADTNIAMIHA ADKRVHSIRE AYLPELSVIP GVNAAIFEEL EGRIFTAFSL YDARNVIKNG 991                 q                                         t              f                                  1080
Alternate
Consensus   DFNNGLSCWN VKGHVDVEEQ NNHRSVLVVP EWEAEVSQEV RVCPGRGYIL RVTAYKEGYG EGCVTIHEIE NNTDELKFSN CVEEEVYPNN 1081       n    g a    c    et g   y      v                                              q                     1170
Alternate
Consensus   TVTCNDYTAT QEEYEGTYTS RNRGYDGAYE SNSSVPADYA SAYEEKAYTD GRRDNPCESN RGYGDYTPLP AGYVTKELEY FPETDKVWIE 1171       1191
Consensus   IGETEGTFIV DSVELLIMEE -
```

BACILLUS THURINGIENSIS δ-ENDOTOXIN

This application claims priority under 35 USC§ 371 to PCT/US95/05090, May 5, 1995 which is a continuation in part of 08/239,474 filed May 6, 1994, now U.S. Pat. No. 5,593,881.

BACKGROUND OF THE INVENTION

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering these B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] *TIBTECH* 6:S4–S7). Thus, isolated B.t. endotoxin genes are becoming commercially valuable.

Until the last ten years, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered B.t. pesticides with specificities for a much broader range of pests. For example, other species of B.t., namely *israelensis* and *tenebrionis* (a.k.a. B.t. M-7, a.k.a. B.t. *san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of B.t. have been identified, and genes responsible for encoding active δ-endotoxin proteins have been isolated (Höfte, H., H. R. Whiteley [1989] *Microbiological Reviews* 52(2):242–255). Höfte and Whiteley classified B.t. crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a B.t. crystal protein gene in *Escherichia coli* has been described in the published literature (Schnepf, H. E., H. R. Whiteley [1981] *Proc. Natl. Acad. Sci. USA* 78:2893–2897). U.S. Pat. No. 4,448,885 and U.S. Pat. No. 4,467,036 both disclose the expression of B.t. crystal protein in *E. coli*. Hybrid B.t. crystal proteins have been constructed that exhibit increased toxicity and display an expanded host range to a target pest. See U.S. Pat. Nos. 5,128,130 and 5,055,294. U.S. Pat. Nos. 4,797,276 and 4,853,331 disclose *B. thuringiensis* strain *tenebrionis* (a.k.a. M-7, a.k.a. B.t. *san diego*) which can be used to control coleopteran pests in various environments. U.S. Pat. No. 4,918,006 discloses B.t. toxins having activity against dipterans. U.S. Pat. No. 4,849,217 discloses B.t. isolates which have activity against the alfalfa weevil. U.S. Pat. No. 5,208,017 discloses coleopteran-active *Bacillus thuringiensis* isolates. U.S. Pat. No. 5,151,363 and U.S. Pat. No. 4,948,734 disclose certain isolates of B.t. which have activity against nematodes. As a result of extensive research and investment of resources, other patents have issued for new B.t. isolates and new uses of B.t. isolates. However, the discovery of new B.t. isolates and new uses of known B.t. isolates remains an empirical, unpredictable art.

A majority of *Bacillus thuringiensis* δ-endotoxin crystal protein molecules are composed of two functional segments. The protease-resistant core toxin is the first segment and corresponds to about the first half of the protein molecule. The three-dimensional structure of a core segment of a cryIIIA B.t. δ-endotoxin is known and it is proposed that all related toxins have that same overall structure (Li, J., J. Carroll, D. J. Ellar [1991] *Nature* 353:815–821). The second half of the molecule is the second segment. For purposes of this application, this second segment will be referred to herein as the "protoxin segment." The protoxin segment is believed to participate in toxin crystal formation (Arvidson, H., P. E. Dunn, S. Strand, A. I. Aronson [1989] *Molecular Microbiology* 3:1533–1534; Choma, C. T., W. K. Surewicz, P. R. Carey, M. Pozsgay, T. Raynor, H. Kaplan [1990] *Eur. J. Biochem.* 189:523–527). The full toxin molecule is rapidly processed to the resistant core segment by protease in the insect gut. The protoxin segment may thus convey a partial insect specificity for the toxin by limiting the accessibility of the core to the insect by reducing the protease processing of the toxin molecule (Haider, M. Z., B. H. Knowles, D. J. Ellar [1986] *Eur. J. Biochem.* 156:531–540) or by reducing toxin solubility (Aronson, A. I., E. S. Han, W. McGaughey, D. Johnson [1991] *Appl. Environ. Microbiol.* 57:981–986).

Chimeric proteins joined within the toxin domains have been reported between CryIC and CryIA(b) (Honee, G., D. Convents, J. Van Rie, S. Jansens, M. Perferoen, B. Visser [1991] *Mol. Microbiol.* 5:2799–2806); however, the activity of these chimeric proteins was either much less, or undetectable, when compared to CryIC on a relevant insect.

Honee et al. (Honee, G., W. Vriezen, B. Visser [1990] *Appl. Environ. Microbiol.* 56:823–825) also reported making a chimeric fusion protein by linking tandem toxin domains of CryIC and CryIA(b). The resulting protein had an increased spectrum of activity equivalent to the combined activities of the individual toxins; however, the activity of the chimeric was not increased toward any one of the target insects.

BRIEF SUMMARY OF THE INVENTION

The subject invention concerns the discovery that the activity of a *Bacillus thuringiensis* (B.t.) δ-endotoxin can be substantially improved by replacing native protoxin amino acids with an alternate protoxin sequence, yielding a chimeric toxin. In a specific embodiment of the subject invention, a chimeric toxin is assembled by substituting all or part of the cryIA(b) protoxin segment for all or part of the native cryIC protoxin segment. The cryIC/cryIA(b) chimeric toxin demonstrates an increased toxicity over the cryIC/cryIC toxin produced by the native gene.

One aspect of the subject invention pertains to genes which encode the advantageous chimeric toxins. Specifically exemplified is a gene comprising DNA encoding the cryIC core N-terminal toxin portion of the chimeric toxin and the cryIA(b) C-terminal protoxin portion of the toxin.

The subject invention further pertains to the use of the chimeric toxin, or microbes containing the gene encoding the chimeric toxin, in methods for controlling lepidopteran pests. The subject invention also includes use of the chimeric gene encoding the claimed toxin. The chimeric gene can be introduced into a wide variety of microbial or plant hosts. A transformed host expressing the chimeric gene can be used to produce the lepidopteran-active toxin of the subject invention. Transformed hosts can be used to produce the insecticidal toxin or, in the case of a plant cell transformed to produce the toxin, the plant will become resistant to insect attack.

Still further, the invention includes the treatment of substantially intact recombinant cells producing the chimeric toxin of the invention. The cells are treated to prolong the lepidopteran activity when the substantially intact cells are applied to the environment of a target pest. Such treatment can be by chemical or physical means, or a combination of chemical and physical means, so long as the chosen means do not deleteriously affect the properties of the pesticide, nor diminish the cell's capability of protecting the pesticide. The treated cell acts as a protective coating for the pesticidal toxin. The toxin becomes active upon ingestion by a target insect.

BRIEF DESCRIPTION OF THE DRAWINGS

FIG. 6—The single letter amino acid code for a chimeric toxin of the subject invention (consensus) with alternate amino acids shown for specific residues.

BRIEF DESCRIPTION OF THE SEQUENCES

Figure 1:
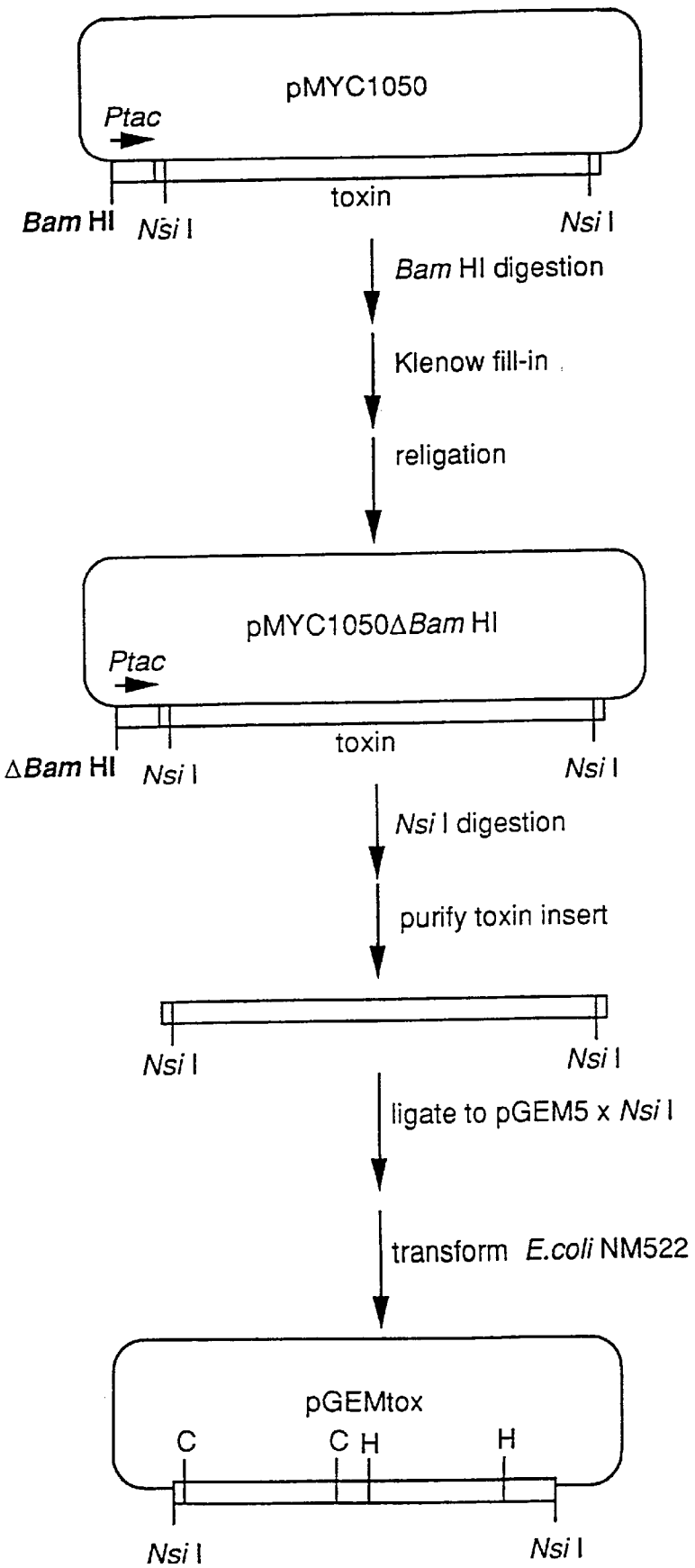
FIG. 1—The BamHI site is removed from pMYC1050 by a fill-in reaction with Klenow polymerase to give plasmid pMYC1050ΔBamHI. To facilitate cloning, an NsiI DNA fragment that contains most of the toxin open reading frame is cloned into pGEM5. The resulting plasmid is called pGEMtox. C=ClaI, H=HindIII.

SEQ ID NO. 1 is oligonucleotide primer "A"
SEQ ID NO. 2 is oligonucleotide primer "B"
SEQ ID NO. 3 is oligonucleotide primer "C"
SEQ ID NO. 4 is oligonucleotide primer "D"
SEQ ID NO. 5 is oligonucleotide primer "E"
SEQ ID NO. 6 is oligonucleotide primer "F"
SEQ ID NO. 7 is oligonucleotide primer "G"
SEQ ID NO. 8 is oligonucleotide primer "L"
SEQ ID NO. 9 is oligonucleotide primer "N"
SEQ ID NO. 10 is oligonucleotide primer "O"
SEQ ID NO. 11 shows an amino acid sequence for a chimeric toxin of the subject invention.
SEQ ID NO. 12 shows an alternate amino acid sequence for a chimeric toxin of the subject invention.
SEQ ID NO. 13 is a characteristic sequence of cryI toxins. This sequence ends at residue 616 of SEQ ID NO. 11.

DETAILED DISCLOSURE OF THE INVENTION

The subject invention concerns the discovery of highly active chimeric *Bacillus thuringiensis* toxins. These chimeric toxins are created by replacing all or part of the native protoxin segment of a full length B.t. toxin with an alternate protoxin segment. In a preferred embodiment, the chimeric toxin comprises a cryIA(b) C-terminal protoxin portion and a cryIC core N-terminal toxin portion. As used herein, reference to a "core" toxin portion refers to the portion of the full length B.t. toxin, other than the protoxin, which is responsible for the pesticidal activity of the toxin.

*Bacillus thuringiensis* strains and other bacteria harboring plasmids useful according to the subject invention are the following:

| Culture | Repository No. | U.S. Pat. No. |
|---|---|---|
| *Bacillus thuringiensis* strain PS81I | NRRL B-18484 | 5,273,746 |
| *Escherichia coli* NM522 (pMYC 394) | NRRL B-18500 | 5,126,133 |
| *Pseudomonas fluorescens* (pM3, 130-7) | NRRL B-18332 | 5,055,294 |
| *Pseudomonas fluorescens* MR436 (pM2, 16-11, aka pMYC436) | NRRL B-18292 | 5,128,130 |

It should be understood that the availability of a deposit does not constitute a license to practice the subject invention in derogation of patent rights granted by governmental action.

The flow charts of FIGS. 1-4 provide a general overview of vector construction that can be carried out according to the subject invention. BamHI and PvuI cloning sites were introduced into a cryIA(c)/cryIA(b) chimeric toxin gene by mutagenesis using the PCR technique of Splice Overlap Extension (SOE) (Horton, R. M., H. D. Hunt, S. N. Ho, J. K. Pullen, L. R. Pease [1989] *Gene* 77:61–68) to give plasmid pMYC2224. A region of the cryIC gene from a cryIC-containing plasmid such as pMYC394 can be generated by PCR and substituted for the BamHI-PvuI cryIA(c)/cryIA(b) gene fragment of pMYC2224. A plasmid created in this manner, pMYC2238, consisted of a short segment of cryIA(c) followed by cryIC to the toxin/protoxin segment junction. The protoxin segment was cryIA(b) from pMYC1050. Fragments of plasmid pMYC2238, plasmid pMYC1197, and a cryIC portion of plasmid pMYC394 were ligated to construct a chimeric gene encoding the toxin of the subject invention. The chimeric gene encodes the claimed toxin comprising a cryIC core N-terminal toxin portion and a cryIA(b) C-terminal protoxin portion which has increased lepidopteran activity compared to a native cryIC toxin.

The chimeric toxins of the subject invention comprise a full core N-terminal toxin portion of a B.t. toxin and, at some point past the end of the toxin portion, the protein has a transition to a heterologous protoxin sequence. The transition to the heterologous protoxin segment can occur at approximately the toxin/protoxin junction or, in the alternative, a portion of the native protoxin (extending past the toxin portion) can be retained with the transition to the heterologous protoxin occurring downstream. As an example, one chimeric toxin of the subject invention has the full toxin portion of cryIC (amino acids 1–616), a portion of the native cryIC protoxin (amino acids 617 to 655), and a heterologous portion of the protoxin (amino acids 656 to the C-terminus). In a preferred embodiment, the heterologous portion of the protoxin is derived from a cryIA(b) toxin.

A person skilled in this art will appreciate that B.t. toxins, even within a certain class such as cryIC, will vary to some extent in length and the precise location of the transition from toxin portion to protoxin portion. Typically, the cryIA (b) and cryIC toxins will be about 1150 to about 1200 amino acids in length. The transition from toxin portion to protoxin portion will typically occur at between about 50% to about 60% of the full length toxin. The chimeric toxin of the subject invention will include the full expanse of this core N-terminal toxin portion. Thus, the chimeric toxin will comprise at least about 50% of the full length B.t. toxin. This will typically be at least about 600 amino acids. With regard to the protoxin portion, the full expanse of the cryIA(b) protoxin portion extends from the end of the toxin portion to the C-terminus of the molecule. It is the last about 100 to 150 amino acids of this portion which are most critical to include in the chimeric toxin of the subject invention. In a chimeric toxin specifically exemplified herein, at least amino acids 1085 to the C-terminus of the cryIA(b) molecule are utilized. Thus, it is at least the last approximately 5 to 10% of the overall B.t. protein which should comprise heterologous DNA (compared to the cryIf core N-terminal toxin portion) included in the chimeric toxin of the subject invention. Thus, a preferred embodiment of the subject invention is a chimeric B.t. toxin of about 1150 to about 1200 amino acids in length, wherein the chimeric toxin comprises a cryIC core N-terminal toxin portion of at least about 50 to 60% of a full cryIC molecule, but no more than about 90 to 95% of the full molecule. The chimeric toxin further comprises a cryIA(b) protoxin C-terminal portion which comprises at least about 5 to 10% of the cryIA(b) molecule. The transition from cryIC to cryIA(b) sequence thus occurs within the protoxin segment (or at the junction of the toxin and protoxin segments) between about 50% and about 95% of the way through the molecule. In the specific example provided herein, the transition from the cryIC sequence to the cryIA (b) sequence occurs prior to amino acid 1085 of the chimeric toxin.

A specific embodiment of the subject invention is the chimeric toxin of SEQ ID NO. 11. Other constructs may be made and used by those skilled in this art having the benefit of the teachings provided herein. The core toxin segment of cryI proteins characteristically ends with the sequence: Val/Leu Tyr/Ile Ile Asp Arg/Lys Ile/Phe Glu Ile/Phe Ile/Leu/ Val Pro/Leu Ala/Val Glu/Thr/Asp (SEQ ID NO. 13), which ends at residue 616 of SEQ ID NO. 11. Additionally, the protoxin segments of the cryI toxins (following residue 616 of SEQ ID NO. 11) bear more sequence similarity than the toxin segments. Because of this sequence similarity, the transition point in the protoxin segment for making a chimeric protein between the cryIC sequence and the cryIA(b) sequence can be readily determined by one skilled in the art. From studies of data regarding the partial proteolysis of CryI genes, the heterogeneity and least-conserved amino acid regions are found after the conserved cryI protoxin sequence, positions 1077–1084 of FIG. 6 or SEQ ID NO. 12 (or 1050–1057 of SEQ ID NO. 11).

Therefore a chimeric toxin of the subject invention can comprise the full cryIC toxin and a portion of the cryIC protoxin, transitioning to the corresponding cryIA(b) sequence at any position between the end of the toxin segment (as defined above) and about position 1084. Preferably, the amino acids which correspond to positions 1085 through 1190 (FIG. 6 or SEQ ID NO. 12; 1058–1163 of SEQ ID NO. 11) comprise a cryIA(b) sequence or equivalent thereof.

CryIC toxins, and genes which encode these toxins, are well known in the art. CryIC genes and toxins have been described in, for example, U.S. Pat. No. 5,188,960 (gene designated 81IB2); Honee et al. (1988) *Nucleic Acids Res.* 16:6240; and Sanchis et al. (1988) *Mol. Microbiol.* 2:393. Also, various cryIA(b) toxins are well known in the art. CryIA(b) genes and toxins have been described in, for example, Höfte et al. (1986) *Eur. J. Biochem.* 161:273; Geiser et al. (1986) *Gene* 48:109; and Haider et al. (1988) *Nucleic Acids Res.* 16:10927. The skilled artisan having the benefit of the teachings contained herein could readily identify and use DNA which encodes the toxin N-terminal portion of a cryIC molecule and the C-terminal protoxin portion of the cryIA(b) toxins.

FIG. 6 provides examples of amino acid substitutions which can be used in the toxins of the subject invention. It is also well known in the art that various mutations can be made in a toxin sequence without changing the activity of a toxin. Furthermore, due to the degeneracy of the genetic code, a variety of DNA sequences can be used to encode a particular toxin. These alternative DNA and amino acid sequences can be used according to the subject invention by a person skilled in this art.

The protoxin substitution techniques of the subject invention can be used with other classes of B.t. endotoxins to enhance processing of the full-length toxin to obtain the active toxin portion which can have enhanced or expanded activity. The technique would be most applicable to other B.t. toxins which have the characteristic sequence shown in SEQ ID NO. 13.

The subject invention not only includes the novel chimeric toxins and the genes encoding these toxins but also includes uses of these novel toxins and genes. For example, the gene of the subject invention may be used to transform host cells. These host cells expressing the gene and producing the chimeric toxin may be used in insecticidal compositions or, in the case of a transformed plant cell, in conferring insect resistance to the transformed cell itself.

Genes and toxins

The genes and toxins useful according to the subject invention include not only the full length sequences disclosed but also fragments of these sequences, variants, and mutants which retain the characteristic pesticidal activity of the toxin specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

It should be apparent to a person skilled in this art that genes encoding active toxins can be identified and obtained through several means. The cryIC and cryIA(b) specific genes (or portions thereof which encode toxin or protoxin domains) useful according to the subject invention may be obtained from the recombinant isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 can be used to systematically cut off nucleotides from the ends of these genes. Alternatively, site-directed mutagenesis can be used. Also, genes which encode active fragments may be obtained using a variety of restriction enzymes. Proteases may be used to directly obtain active fragments of these toxins.

Fragments and equivalents which retain the pesticidal activity of the exemplified toxin would be within the scope of the subject invention. Also, as bote above, because of the redundancy of the genetic code, a variety of different DNA sequences can encode the amino acid sequence disclosed herein. It is well within the skill of a person trained in the art to create these alternative DNA sequences encoding the same, or essentially the same, toxin. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying additional toxins and genes useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) *DNA Probes,* Stockton Press, New York, N.Y., pp. 169–170. Detection of the probe provides a means for determining in a known manner whether hybridization has occurred. Such a probe analysis provides a rapid method for identifying toxin-encoding genes useful according to the subject invention. Preferably, such genes would be cryIC genes whose core toxin-encoding N-terminal portions can be used with a cryIA(b) protoxin-encoding C-terminal portion to create a chimeric gene according to the subject invention. The nucleotide segments which are used as probes according to the invention can be synthesized using DNA synthesizer and standard procedures. These nucleotide sequences can also be used as PCR primers to amplify genes of the subject invention.

Certain chimeric toxins of the subject invention have been specifically exemplified herein. It should be readily apparent that the subject invention comprises variant or equivalent toxins (and nucleotide sequences encoding equivalent toxins) having the same or similar pesticidal activity of the exemplified toxin. Equivalent toxins will have amino acid homology with the exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same class fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant Hosts

A gene encoding the chimeric toxins of the subject invention can be introduced into a wide variety of microbial or plant hosts. Expression of the toxin gene results, directly or indirectly, in the intracellular production and maintenance of the pesticidal chimeric toxin. With suitable microbial hosts, e.g., Pseudomonas, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the gene encoding the chimeric toxin is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a gene encoding a chimeric toxin into a microorganism host under conditions which allow for the stable maintenance and expression of the gene. These methods are well known to those skilled in the art and are described, for example, in U.S. Pat. No. 5,135,867, which is incorporated herein by reference.

Treatment of cells

As mentioned above, recombinant cells producing the chimeric toxin of the subject invention can be treated to prolong the toxic activity and stabilize the cell. The pesticide microcapsule that is formed comprises the B.t. toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the gene encoding a chimeric toxin of the subject invention, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques,* W.H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Since the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells

The cellular host containing the gene encoding a chimeric toxin of the subject invention may be grown in any convenient nutrient medium, where the DNA construct provides a selective advantage, providing for a selective medium so that substantially all or all of the cells retain the recombinant gene. These cells may then be harvested in accordance with conventional methods. Alternatively, the cells can be treated prior to harvesting.

Formulations

Recombinant microbes comprising the gene encoding the chimeric toxin disclosed herein, can be formulated into bait granules and applied to the soil. Formulated product can also be applied as a seed-coating or root treatment or total plant treatment at later stages of the crop cycle. Plant and soil treatments may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Materials and Methods

NACS (Bethesda Research Labs, Gaithersburg, Md.) column chromatography was used for purification of electroeluted DNA. Purification was performed according to manufacturer's instructions with the exception that binding buffers were modified to 0.5X TBE/0.2 M NaCl and elution buffers were modified to 0.5X TBE/2.0 M NaCl.

Random primer labeling of DNA with $^{32}$P was done with a kit (Boehringer-Mannheim Biochemicals, Indianapolis, Ind.) according to manufacturer's instructions.

Gel purification refers to the sequential application of agarose-TBE gel electrophoresis, electroelution, and NACS column chromatography for the purification of selected DNA fragments, these methods are well known in the art.

Polymerase chain reaction (PCR) amplification of DNA was done for 25 cycles on a Perkin Elmer (Norwalk, Conn.) thermal cycler with the following cycle parameters: 94° C. for 1 minute, 37° C. for 2 minutes, 72° C. for 3 minutes (each 72° C. cycle has a 5 second extension time). PCR products were treated with proteinase K to improve cloning efficiency (Crowe, J. S., Cooper, H. J., Smith, M. A., Sims, M. J., Parker, D., Gewert, D. [1991] *Nucl. Acids Res.* 19:184).

Oligodeoxyribonucleotides (oligonucleotides) were synthesized on an Applied Biosystems (Foster City, Calif.) model 381A DNA synthesizer. Purification was done, when necessary, on Nensorb columns (New England Nuclear-Dupont, Wilmington, Del.), according to the manufacturer's instructions.

Following are examples which illustrate procedures, including the best mode, for practicing the invention. These examples should not be construed as limiting. All percentages are by weight and all solvent mixture proportions are by volume unless otherwise noted.

EXAMPLE 1

Expression Vector Modification by Splice Overlap Extension

A cloning vector can be constructed based upon pMYC1050, a broad host-range plasmid derived from RSF1010 (pTJS260 can be obtained from Dr. Donald Helinski, U.C. San Diego). An example of the system used in the vector construction may be found in EPO patent application 0 471 564. Plasmid DNA of pMYC1050 initially contained the chimeric toxin gene cryIA(c)/cryIA(b). The toxin encoded by this gene is described in U.S. Pat. No. 5,055,294. pMYC1050 was constructed by re-cloning the toxin gene and promoter of pM3,130-7 (disclosed in U.S. Pat. No. 5,055,294) into a pTJS260-based-vector such as pMYC467 (disclosed in U.S. Pat. No. 5,169,760) by methods well known in the art. In particular, the pM3,130-7 promoter and toxin gene can be obtained as a BamHI to NdeI fragment and placed into the pMYC467 plasmid, replacing a fragment bounded by the same sites (BamHI near base 12100 and NdeI near base 8000).

The improved vector ideally contains a unique BamHI cloning site. The plasmid BamHI site, located upstream from the tac promoter (ptac), can be removed by blunting with Klenow and re-ligating (FIG. 1). Absence of the site was confirmed by restriction digestion. A plasmid produced according to this procedure was called pMYC1050ΔBamHI. The construct can now have of a BamHI site added to the plasmid by SOE mutagenesis. SOE mutagenesis can be facilitated by subcloning an NsiI toxin-containing DNA fragment from the plasmid into the smaller pGEM5 (Promega Corp., Madison, Wis.) vector which uses the bla gene as a selectable marker (FIG. 1). The fragment can be oriented by restriction digestion. A plasmid produced according to this procedure was called pGEMtox.

Figure 2:
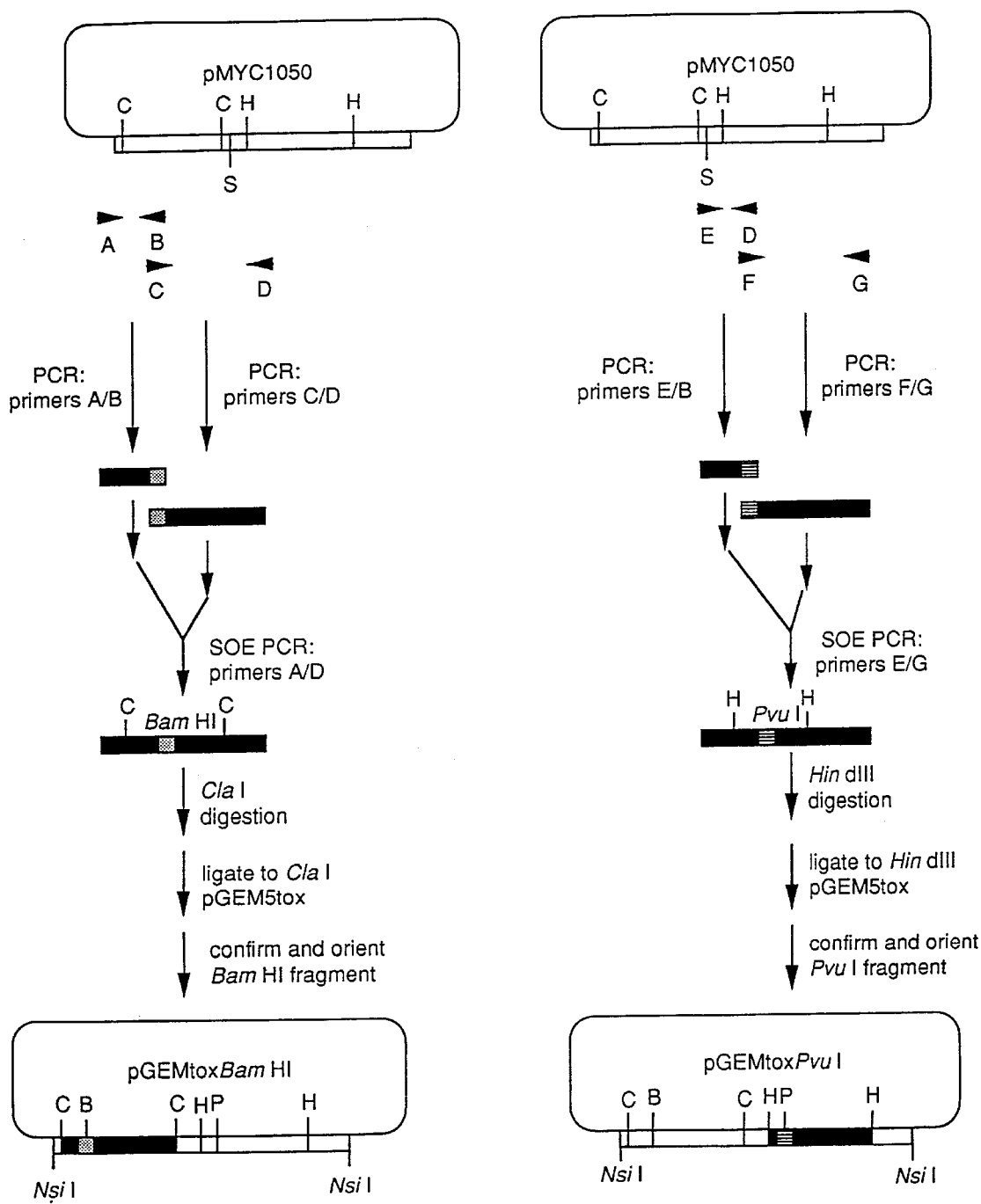
FIG. 2—BamHI or PvuI cloning sites were introduced into toxin DNA by the technique of Splice Overlap Extension (SOE). DNA fragments with the new sites are used to replace homologous DNA fragments in pGEMtox. The resulting plasmids are pGEMtox BamHI or pGEMtox PvuI. The letters A through G below the arrows correspond to oligonucleotide primers in the text. Letters above vertical lines correspond to restriction enzyme sites. B=BamHI, C=ClaI, H=HindIII, P=PvuI, S=SacI.
Figure 3:
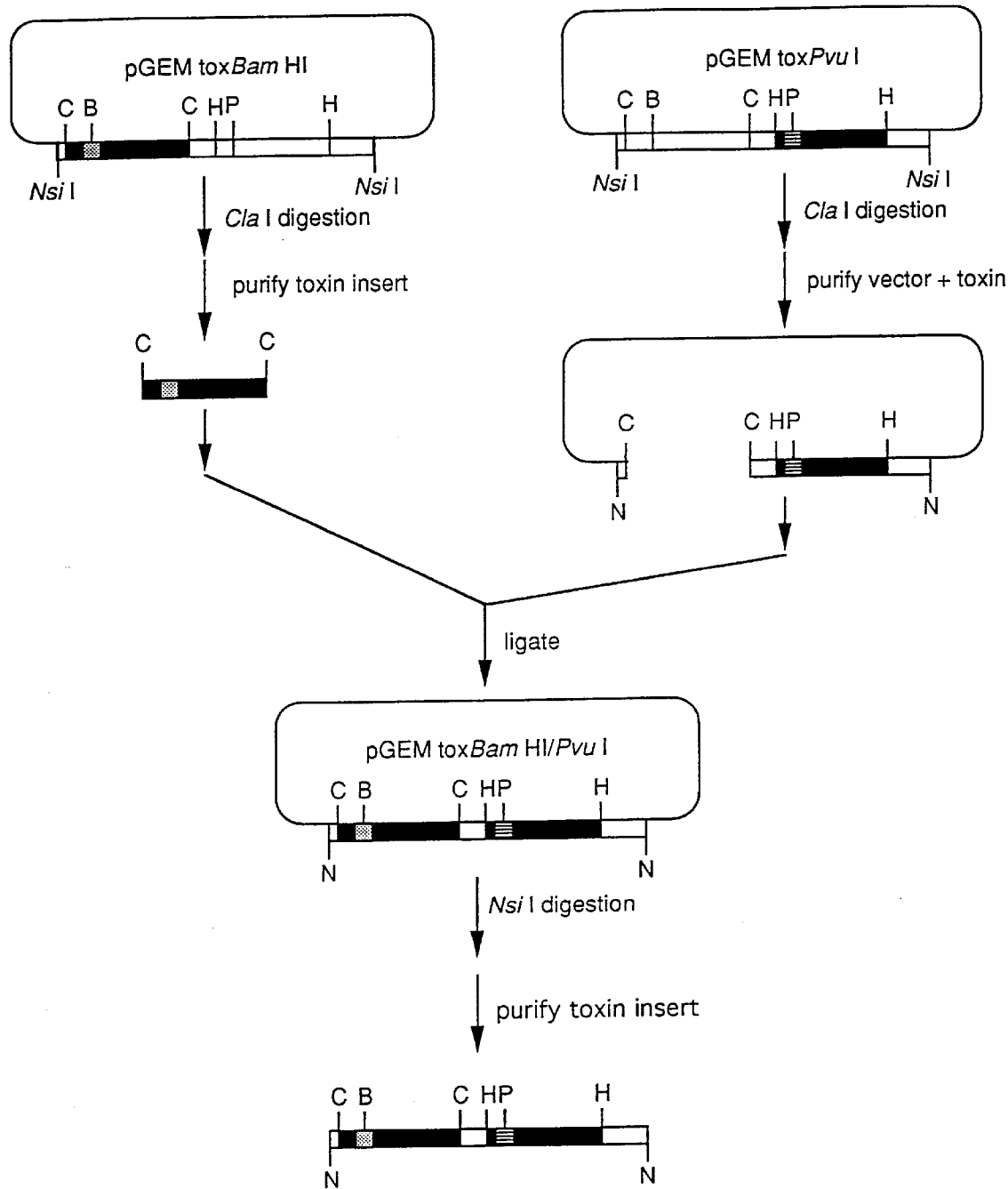
FIG. 3—The DNA fragment containing the BamHI mutation is used to replace the homologous fragment in pGEMtox PvuI. The resulting plasmid which contains both cloning sites is pGEMtox BamHI/PvuI. To construct an expression plasmid, the toxin-containing NsiI fragment is excised for cloning into the pTJS260 broad host-range vector. B=BamHI, C=ClaI, H=HindIII, P=PvuI.
Figure 4:
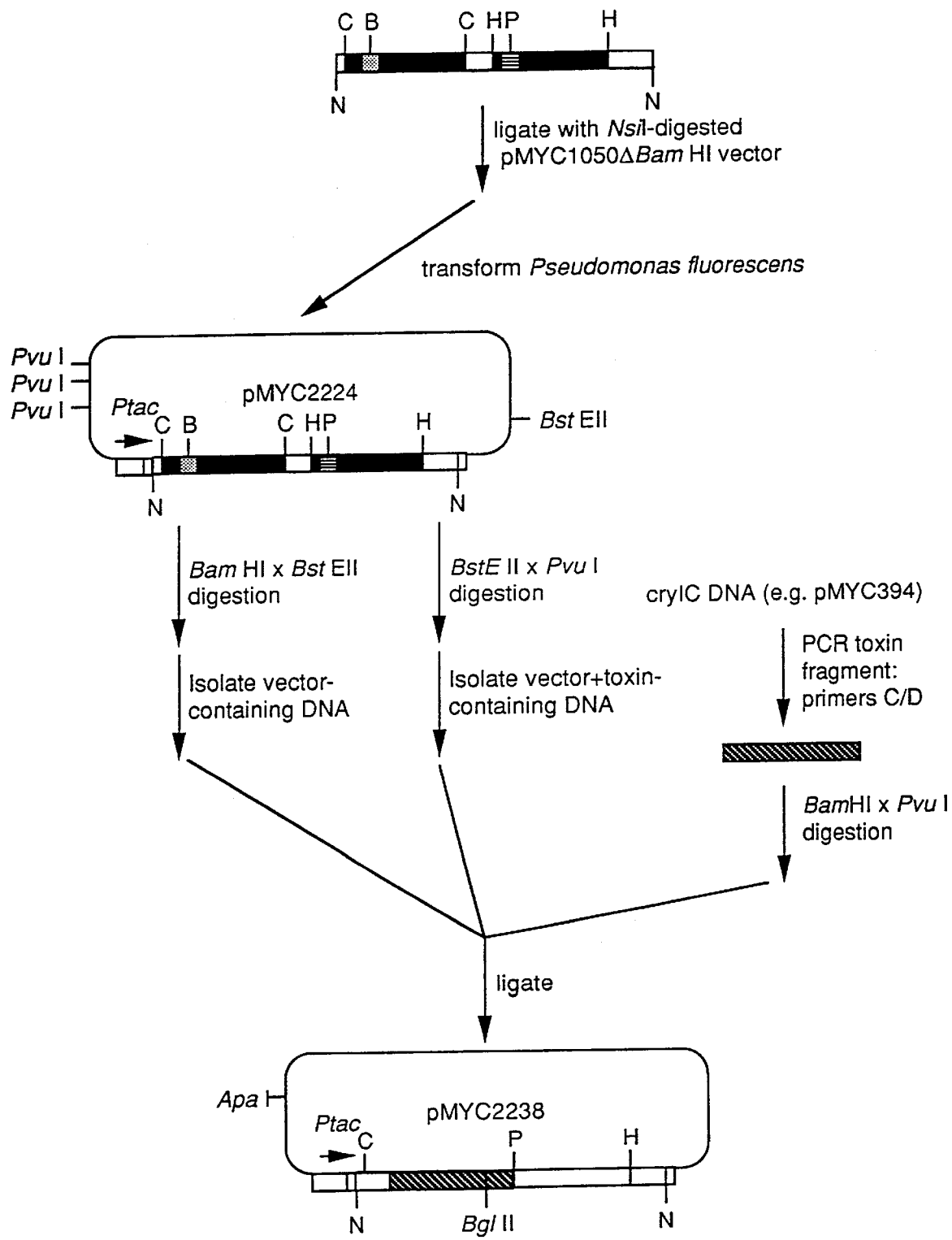
FIG. 4—The NsiI toxin-containing fragment with the new restriction sites is ligated to the vector-containing DNA from pMYC1050ΔBamHI to give pMYC2244. A BamHI-PvuI PCR-derived DNA fragment containing the cryIC toxin is exchanged for the equivalent fragment in pMYC2244. The resulting chimera is called pMYC2238. B=BamHI, C=ClaI, H=HindIII, N=NsiI, P=PvuI.

DNA in the toxin-encoding region was mutated by the PCR-mediated technique of SOE to introduce restriction enzyme cloning sites as shown in FIG. 2. Oligonucleotides used as primers are shown below:

| "A" | (SEQ ID NO. 1) | 5' GCATACTAGTAGGAGATTTCCATGGATAACAATCCGAAC 3' |
| --- | --- | --- |
| "B" | (SEQ ID NO. 2) | 5' GGATCCGCTTCCCAGTCT 3' |
| "C" | (SEQ ID NO. 3) | 5' AGAGAGTGGGAAGCGGATCCTACTAATCC 3' |
| "D" | (SEQ ID NO. 4) | 5' TGGATACTCGATCGATATGATAATCCGT 3' |
| "E" | (SEQ ID NO. 5) | 5' TAATAAGAGCTCCTATGT 3' |
| "F" | (SEQ ID NO. 6) | 5' TATCATATCGATCGAGTATCCAATTTAG 3' |
| "G" | (SEQ ID NO. 7) | 5' GTCACATAGCCAGCTGGT 3' |

Plasmid pMYC1050 DNA was used as the template for PCR amplification using primer sets A/B, C/D, E/D, and F/G. Amplified DNA fragments were named AB, CD, ED, and FG. Amplified DNAs were purified by agarose-TBE gel electrophoresis, electroelution, and NACS column chromatography. Purified template DNAs were used in a second set of PCR reactions. Fragments AB and CD were mixed and amplified with primers A and D. In a separate reaction, fragments ED and FG were mixed and amplified with primers E and G. Amplified DNA was resolved by agarose-TBE gel electrophoresis and the fragments with the corresponding increase in size were excised, electroeluted, and purified. Amplified DNA fragments are called AD or EG for reference.

Figure 5:
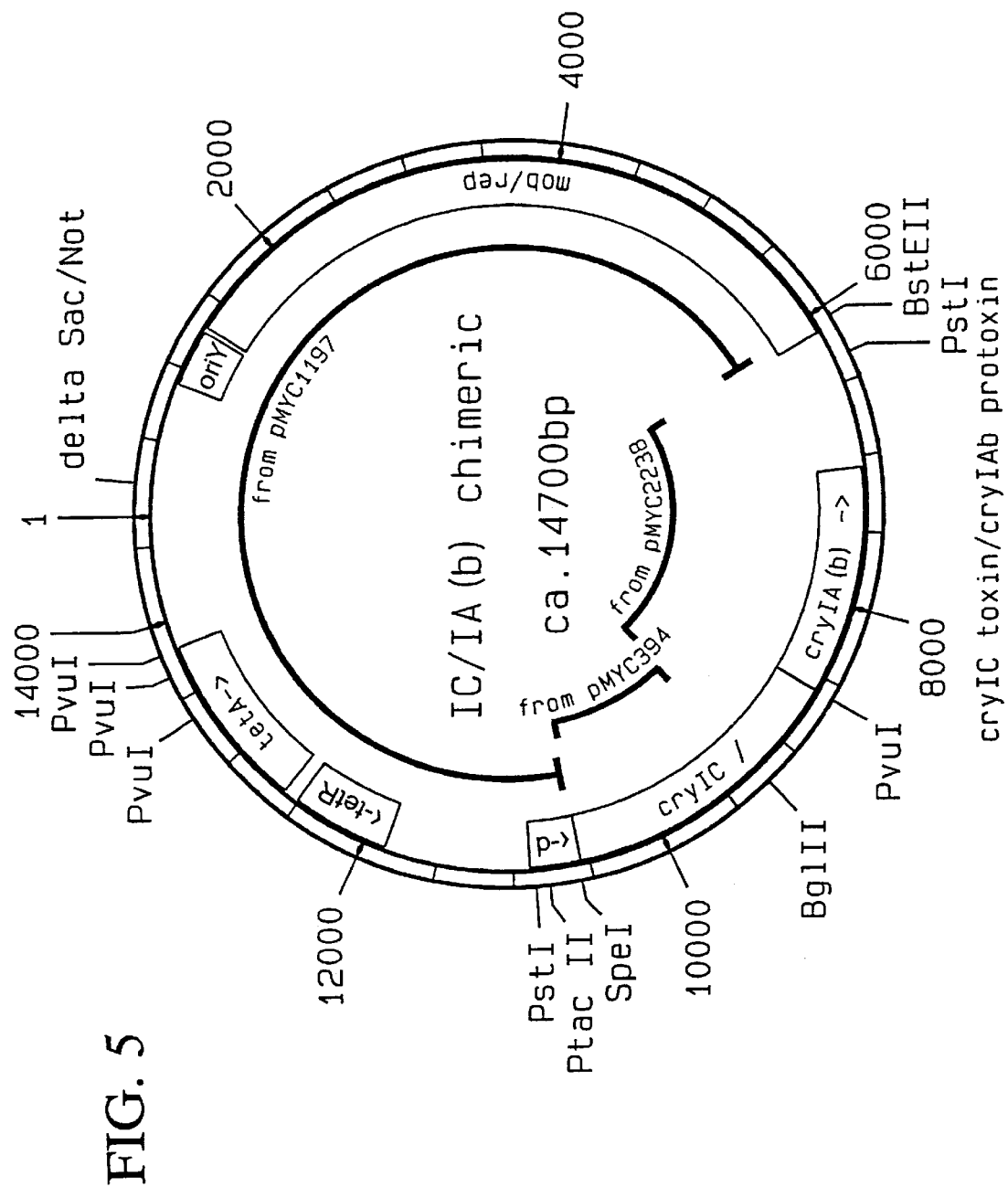
FIG. 5—A restriction map of a plasmid carrying a chimeric gene of the subject invention.

DNA fragments AD or EG with the new restriction enzyme sites were incorporated into the toxin-containing DNA by several subcloning experiments (FIGS. 2 and 3). pGEMtox was digested with ClaI or HindIII. Vector toxin-containing DNA was gel-purified. Fragment AD was digested with ClaI and ligated to ClaI-digested pGEMtox vector DNA. Fragment EG was digested with HindIII and ligated to HindIII-digested pGEMtox vector DNA. *E. coli* strain NM522 was transformed with ligation mixes. Correctly assembled constructs were identified by restriction enzyme digestion of plasmid DNA from isolated colonies. The plasmid with the new BamHI site was called pGEMtox BamHI. The plasmid with the new PvuI site was called pGEMtox PvuI. The ClaI fragment containing the BamHI site from plasmid pGEMtox BamHI was ligated to the phosphatased ClaI vector-containing fragment from pGEMtox PvuI. *E. coli* strain NM522 was transformed with ligation mixes. Correctly assembled constructs were identified by PCR analysis with primer set C/D, and by restriction digestion. The plasmid with both new restriction enzyme sites was called pGEMtox BamHI/PvuI.

A completed expression vector was assembled with the insert from pGEMtox BamHI/PvuI and the vector from pMYC1050ΔBamHI (FIGS. 3 and 4). Gel-purified insert was prepared from pGEMtox BamHI/PvuI by NsiI digestion, and ScaI digestion (to remove contaminating vector). It was ligated to gel-purified NsiI-digested vector-containing pMYC1050ΔBamHI DNA. *E. coli* strain NM522 was transformed with the ligation mixes, and transformation mixes were plated on LB agar containing tetracycline at 12 μg/ml. Colonies containing the NsiI insert were identified by colony hybridization and autoradiography. Inserts were oriented by PCR, using primer set A/D, which bridges a NsiI cloning site, and agarose-TBE gel electrophoresis. The correctly assembled plasmid is called pMYC2224. A lactose-inducible *P. fluorescens* strain was electroporated with correctly assembled plasmid DNA. Transformation mixes were plated on LB agar containing tetracycline at 20 μg/ml. Plasmid DNA was prepared from *P. fluorescens* for use in subsequent cloning experiments.

EXAMPLE 2

Subcloning the cryIC Hypervariable Region into pMYC2224

A DNA fragment containing the hypervariable region of the cryIC gene is obtained by PCR using primers C and D (SEQ ID NOS. 3 and 4, respectively, from *Bacillus thuringiensis* DNA (e.g., PS81I) or a plasmid with cloned DNA (e.g., pMYC394) containing cryIC. The resulting PCR fragment was digested with restriction enzymes BamHI and PvuI and purified following agarose gel electrophoresis. Since the tetAR gene contains multiple PvuI sites, it was necessary to isolate the vector-containing DNA on two separate fragments. To obtain the first fragment, pMYC2224 was digested with BamHI×BstEII, and the large DNA fragment containing the promoter-tetAR locus-rep functions was gel-purified. To obtain the second fragment, pMYC2224 was digested with BstEII×PvuI, and the DNA fragment containing the vector-protoxin module was gel-purified. A three-piece ligation was set up and used for *E. coli* strain NM522 transformation. Plasmids were recovered following transformation of *E. coli* containing the correct inserts, as judged by restriction enzyme digestion.

The correct plasmid is named pMYC 2238. The plasmid consists of cryIA(c) at the amino-terminus, cryIC up to the toxin/protoxin junction, and cryIA(b) through the protoxin segment.

EXAMPLE 3

Construction of a Native cryIC and a Chimeric cryIC/cryIA(b) Protoxin Expression Plasmids An expression plasmid containing the cryIC gene can be constructed using a three-fragment ligation as follows: (1) digestion of pMYC394 (from NRRL B-18500) with HindIII with subsequent purification of a ≈600 bp fragment containing the cryIC gene; (2) digestion of pTJS260, from which the SacI (bp 214) to NotI (bp 1674) had been deleted (described in EP 0 471 564 A2) with EcoRI and HindIII with subsequent purification of the ≈6300 bp fragment containing the plasmid replication origin; (3) digestion of pMYC1197 (described in EP 0 471 564 A2) with EcoRI and SpeI followed by purification of an ≈4200 bp fragment containing the tetracycline resistance genes and ptac promoter. The three fragments are ligated together and transformed into a lactose-inducible *P. fluorescens* using electroporation. The resulting tetracycline-resistant colonies are screened for plasmids having the correct structure.

An expression plasmid containing the cryIC/cryIA(b) chimeric gene can be constructed by digesting pMYC2238 with BglII and BstEII and purifying the ≈3200 bp fragment. A second fragment can be produced by digesting the cryIC expression plasmid above with the same enzymes and subsequent purification of an ≈12000 bp fragment. The fragments are ligated together and transformed into a lactose-inducible *P. fluorescens* using electroporation. The resulting tetracycline-resistant colonies are screened for plasmids having the structure indicated in FIG. 5 by restriction enzyme digestion and agarose gel analysis.

U.S. Pat. No. 5,169,760 discloses means for making *P. fluorescens* capable of regulating β-galactoside-inducible promoters. This patent and EP 0 471 564 A2 describe conditions for expression of these genes in *P. fluorescens*.

EXAMPLE 4

Activity of the Chimeric Toxin Against *Spodoptera exigua*

Serial dilutions of recombinant *Pseudomonas fluorescens* stabilized by the methods disclosed in U.S. Pat. Nos. 4,695,455 and 4,695,462 were mixed with modified USDA soy flour insect diet (Technical Bulletin 1528, U.S. Department of Agriculture). This mixture was poured into plastic trays with compartmentalized 3-ml wells (Nutrend Container Corporation, Jacksonville, Fla.). Water served as a control as well as the vehicle to introduce the toxin protein into the diet. Second-instar *Spodoptera exigua* larvae were placed singly onto the diet mixture. Wells were then sealed with MYLAR sheeting (ClearLam Packaging, Ill.) using a tacking iron, and several pinholes were made in each well to provide gas exchange. Larvae were held with continuous light at 25° C. or 29° C. and mortality was recorded after six or four days, respectively. $LC_{50}$s were determined by standard log-probit analysis (POLO-PC, LeOra Software, 1987). CryIC and the cryIC/cryIA(b) chimeric were tested simultaneously and representative results are as follows:

TABLE 2

| Toxin Designation | LC50 (μg toxin/ml diet) |
|---|---|
| cryIC | 139 |
| cryIC/cryIA(b) | 28 |

EXAMPLE 5

Insertion of the Gene Encoding the Chimeric Toxin Into Plants

One aspect of the subject invention is the transformation of plants with genes encoding the insecticidal toxin. The transformed plants are resistant to attack by the target pest.

The gene encoding the chimeric toxin, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the B.t. toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 0 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed traits to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. Also, advantageously, plants encoding a truncated toxin will be used. The truncated toxin typically will encode about 55% to about 80% of the full length toxin. Methods for creating synthetic genes for use in plants are known in the art.

EXAMPLE 6

Cloning of the Gene Encoding the Chimeric Toxin Into Insect Viruses

A number of viruses are known to infect insects. These viruses include, for example, baculoviruses and entomopoxviruses. In one embodiment of the subject invention, genes encoding the insecticidal toxins, as described herein, can be placed within the genome of the insect virus, thus enhancing the pathogenicity of the virus. Methods for constructing insect viruses which comprise the chimeric toxin gene are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 71:1535–1544) and Martens et al. (Martens, J. W. M., G. Honee, D. Zuidema, J. W. M. van Lent, B. Visser, J. M. Vlak (1990) *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

---

We claim:

1. A substantially pure chimeric *Bacillus thuringiensis* toxin comprising a cryIC core N-terminal toxin portion and a cryIA(b) C-terminal protoxin portion, wherein said chimeric toxin has approximately 1150 to 1200 amino acids, wherein said toxin comprises a cryIC core N-terminal sequence of at least about 600 amino acids and no more than about 1100 amino acids, and wherein the amino acid sequence from the end of said core N-terminal sequence to the C-terminus of the chimeric toxin is a cryIA(b) sequence.

2. The toxin, according to claim 1, wherein said core toxin portion comprises the first about 616 amino acids of a cryIC toxin and wherein said protoxin portion comprises the amino acids from about 1058 of SEQ ID NO. 11 to the C-terminus of the cryIA(b) toxin.

3. The chimeric B.t. toxin, according to claim 1, wherein said toxin has an amino acid sequence shown in SEQ ID NO 12.

4. The chimeric B.t. toxin, according to claim 1, wherein the transition from a cryIC sequence to a cryIA(b) sequence occurs after the sequence shown in SEQ ID NO. 13 and before a sequence corresponding to positions 1050 to 1057 of SEQ ID NO. 11.

5. The toxin, according to claim 1, wherein said toxin has the amino acid sequence shown in SEQ ID NO. 11.

6. Treated, substantially intact cells containing an intracellular toxin, which toxin is a result of expression of a *Bacillus thuringiensis* gene encoding a toxin active against lepidopteran pests wherein said toxin is that of claim 1, wherein said cells are treated under conditions which prolong the insecticidal activity when said cells are applied to the environment of a target insect.

7. The cells, according to claim 6, wherein the cells are treated by chemical or physical means to prolong the insecticidal activity in the environment.

8. A process for controlling lepidopteran pests comprising contacting said pest with a lepidopteran-controlling effective amount of a toxin of claim 1.

* * * * *

UNITED STATES PATENT AND TRADEMARK OFFICE
CERTIFICATE OF CORRECTION

PATENT NO. : 5,932,209
DATED : August 3, 1999
INVENTOR(S) : Thompson *et al.*

It is certified that error appears in the above-identified patent and that said Letters Patent is hereby corrected as shown below:

Column 5, line 64: "CcryIf" should read --cryIF--.

Column 14, line 28: "BamHIxBstEII" should read --BamHI x BstEII--.

Column 14, line 32: "BstEIIxPvuI" should read --BstEII x PvuI--.

Column 14, line 50: "of a ≈ 600 bp" should read --of a ≈ 4600 bp--.

Signed and Sealed this

Twenty-eighth Day of March, 2000

Attest:

Q. TODD DICKINSON

*Attesting Officer*   *Commissioner of Patents and Trademarks*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 39 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:1:

GCATACTAGT AGGAGATTTC CATGGATAAC AATCCGAAC                                    39

(2) INFORMATION FOR SEQ ID NO:2:

(i) SEQUENCE CHARACTERISTICS:
      (A) LENGTH: 18 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:2:

GGATCCGCTT CCCAGTCT                                                          18

(2) INFORMATION FOR SEQ ID NO:3:

(i) SEQUENCE CHARACTERISTICS:
      (A) LENGTH: 29 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:3:

AGAGAGTGGG AAGCGGATCC TACTAATCC                                              29

(2) INFORMATION FOR SEQ ID NO:4:

(i) SEQUENCE CHARACTERISTICS:
      (A) LENGTH: 28 bases
      (B) TYPE: nucleic acid
      (C) STRANDEDNESS: single (D) TOPOLOGY: linear (ii) MOLECULE TYPE: DNA (synthetic)

(xi) SEQUENCE DESCRIPTION: SEQ ID NO:4:

TGGATACTCG ATCGATATGA TAATCCGT                                          28

(2) INFORMATION FOR SEQ ID NO:5:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:5:

TAATAAGAGC TCCTATGT                                                     18

(2) INFORMATION FOR SEQ ID NO:6:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:6:

TATCATATCG ATCGAGTATC CAATTTAG                                          28

(2) INFORMATION FOR SEQ ID NO:7:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:7:

GTCACATAGC CAGCTGGT                                                     18

(2) INFORMATION FOR SEQ ID NO:8:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:8:

GAGTGGGAAG CAGATCTTAA TAATGCACAA TTAAGG                                 36

(2) INFORMATION FOR SEQ ID NO:9:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:9:

```
TTAATCATCG GCTCGTA                                                           17

(2) INFORMATION FOR SEQ ID NO:10:

(i) SEQUENCE CHARACTERISTICS:
         (A) LENGTH: 23 bases
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:10:

ACTCGATCGA TATGATARTC CGT                                                    23

(2) INFORMATION FOR SEQ ID NO:11:

(i) SEQUENCE CHARACTERISTICS:
         (A) LENGTH: 1163 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:11:
```

Met Glu Glu Asn Asn Gln Asn Gln Cys Ile Pro Tyr Asn Cys Leu Ser
1               5                   10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile

-continued

```
                260                 265                 270
Asn Phe Asn Pro Gln Leu Gln Ser Val Ala Gln Leu Pro Thr Phe Asn
            275                 280                 285
Val Met Glu Ser Ser Ala Ile Arg Asn Pro His Leu Phe Asp Ile Leu
    290                 295                 300
Asn Asn Leu Thr Ile Phe Thr Asp Trp Phe Ser Val Gly Arg Asn Phe
305                 310                 315                 320
Tyr Trp Gly Gly His Arg Val Ile Ser Ser Leu Ile Gly Gly Asn
                325                 330                 335
Ile Thr Ser Pro Ile Tyr Gly Arg Glu Ala Asn Gln Glu Pro Pro Arg
            340                 345                 350
Ser Phe Thr Phe Asn Gly Pro Val Phe Arg Thr Leu Ser Asn Pro Thr
            355                 360                 365
Leu Arg Leu Leu Gln Gln Pro Trp Pro Ala Pro Pro Phe Asn Leu Arg
    370                 375                 380
Gly Val Glu Gly Val Glu Phe Ser Thr Pro Thr Asn Ser Phe Thr Tyr
385                 390                 395                 400
Arg Gly Arg Gly Thr Val Asp Ser Leu Thr Glu Leu Pro Pro Glu Asp
                405                 410                 415
Asn Ser Val Pro Pro Arg Glu Gly Tyr Ser His Arg Leu Cys His Ala
            420                 425                 430
Thr Phe Val Gln Arg Ser Gly Thr Pro Phe Leu Thr Thr Gly Val Val
            435                 440                 445
Phe Ser Trp Thr His Arg Ser Ala Thr Leu Thr Asn Thr Ile Asp Pro
    450                 455                 460
Glu Arg Ile Asn Gln Ile Pro Leu Val Lys Gly Phe Arg Val Trp Gly
465                 470                 475                 480
Gly Thr Ser Val Ile Thr Gly Pro Gly Phe Thr Gly Gly Asp Ile Leu
                485                 490                 495
Arg Arg Asn Thr Phe Gly Asp Phe Val Ser Leu Gln Val Asn Ile Asn
            500                 505                 510
Ser Pro Ile Thr Gln Arg Tyr Arg Leu Arg Phe Arg Tyr Ala Ser Ser
            515                 520                 525
Arg Asp Ala Arg Val Ile Val Leu Thr Gly Ala Ala Ser Thr Gly Val
    530                 535                 540
Gly Gly Gln Val Ser Val Asn Met Pro Leu Gln Lys Thr Met Glu Ile
545                 550                 555                 560
Gly Glu Asn Leu Thr Ser Arg Thr Phe Arg Tyr Thr Asp Phe Ser Asn
                565                 570                 575
Pro Phe Ser Phe Arg Ala Asn Pro Asp Ile Ile Gly Ile Ser Glu Gln
            580                 585                 590
Pro Leu Phe Gly Ala Gly Ser Ile Ser Ser Gly Glu Leu Tyr Ile Asp
            595                 600                 605
Lys Ile Glu Ile Ile Leu Ala Asp Ala Thr Phe Glu Ala Glu Ser Asp
    610                 615                 620
Leu Glu Arg Ala Gln Lys Ala Val Asn Ala Leu Phe Thr Ser Ser Asn
625                 630                 635                 640
Gln Ile Gly Leu Lys Thr Asp Val Thr Asp Tyr His Ile Asp Arg Val
                645                 650                 655
Ser Asn Leu Val Glu Cys Leu Ser Asp Glu Phe Cys Leu Asp Glu Lys
            660                 665                 670
Lys Glu Leu Ser Glu Lys Val Lys His Ala Lys Arg Leu Ser Asp Glu
            675                 680                 685
```

```
Arg Asn Leu Leu Gln Asp Pro Asn Phe Arg Gly Ile Asn Arg Gln Leu
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Gly Thr Phe Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Gln Leu Arg Gly Tyr Ile Glu Asp Ser Gln Asp
        755                 760                 765

Leu Glu Ile Tyr Leu Ile Arg Tyr Asn Ala Lys His Glu Thr Val Asn
    770                 775                 780

Val Pro Gly Thr Gly Ser Leu Trp Pro Leu Ser Ala Pro Ser Pro Ile
785                 790                 795                 800

Gly Lys Cys Ala His Ser His His Phe Ser Leu Asp Ile Asp Val
                805                 810                 815

Gly Cys Thr Asp Leu Asn Glu Asp Leu Gly Val Trp Val Ile Phe Lys
            820                 825                 830

Ile Lys Thr Gln Asp Gly His Ala Arg Leu Gly Asn Leu Glu Phe Leu
        835                 840                 845

Glu Glu Lys Pro Leu Val Gly Glu Ala Leu Ala Arg Val Lys Arg Ala
    850                 855                 860

Glu Lys Lys Trp Arg Asp Lys Arg Glu Lys Leu Glu Trp Glu Thr Asn
865                 870                 875                 880

Ile Val Tyr Lys Glu Ala Lys Glu Ser Val Asp Ala Leu Phe Val Asn
                885                 890                 895

Ser Gln Tyr Asp Arg Leu Gln Ala Asp Thr Asn Ile Ala Met Ile His
            900                 905                 910

Ala Ala Asp Lys Arg Val His Ser Ile Arg Glu Ala Tyr Leu Pro Glu
        915                 920                 925

Leu Ser Val Ile Pro Gly Val Asn Ala Ala Ile Phe Glu Glu Leu Glu
    930                 935                 940

Gly Arg Ile Phe Thr Ala Phe Ser Leu Tyr Asp Ala Arg Asn Val Ile
945                 950                 955                 960

Lys Asn Gly Asp Phe Asn Asn Gly Leu Ser Cys Trp Asn Val Lys Gly
                965                 970                 975

His Val Asp Val Glu Glu Gln Asn Asn His Arg Ser Val Leu Val Val
            980                 985                 990

Pro Glu Trp Glu Ala Glu Val Ser Gln Glu Val Arg Val Cys Pro Gly
        995                 1000                1005

Arg Gly Tyr Ile Leu Arg Val Thr Ala Tyr Lys Glu Gly Tyr Gly Glu
    1010                1015                1020

Gly Cys Val Thr Ile His Glu Ile Glu Asn Asn Thr Asp Glu Leu Lys
1025                1030                1035                1040

Phe Ser Asn Cys Val Glu Glu Val Tyr Pro Asn Asn Thr Val Thr
                1045                1050                1055

Cys Asn Asp Tyr Thr Ala Thr Gln Glu Glu Tyr Glu Gly Thr Tyr Thr
            1060                1065                1070

Ser Arg Asn Arg Gly Tyr Asp Gly Ala Tyr Glu Ser Asn Ser Ser Val
        1075                1080                1085

Pro Ala Asp Tyr Ala Ser Ala Tyr Glu Glu Lys Ala Tyr Thr Asp Gly
    1090                1095                1100

Arg Arg Asp Asn Pro Cys Glu Ser Asn Arg Gly Tyr Gly Asp Tyr Thr
1105                1110                1115                1120
```

```
Pro Leu Pro Ala Gly Tyr Val Thr Lys Glu Leu Glu Tyr Phe Pro Glu
            1125                1130                1135

Thr Asp Lys Val Trp Ile Glu Ile Gly Glu Thr Glu Gly Thr Phe Ile
            1140                1145                1150

Val Asp Ser Val Glu Leu Leu Leu Met Glu Glu
            1155                1160
```

(2) INFORMATION FOR SEQ ID NO:12:

(i) SEQUENCE CHARACTERISTICS:
        (A) LENGTH: 1190 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met Glu Glu Asn Asn Gln Asn Gln Cys Ile Pro Tyr Asn Cys Leu Ser
1               5                   10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
            35                  40                  45

Phe Val Pro Gly Gly Gly Phe Leu Val Gly Leu Ile Asp Phe Val Trp
50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
            85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Xaa Asn Pro Xaa Thr Arg Thr Arg
            115                 120                 125

Val Ile Asp Arg Phe Arg Ile Leu Asp Gly Leu Leu Glu Arg Asp Ile
            130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
            165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
            195                 200                 205

Thr Tyr Asn Arg Gly Leu Asn Asn Leu Pro Lys Ser Thr Tyr Gln Asp
            210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
            245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
            275                 280                 285

Val Met Glu Ser Ser Xaa Ile Arg Asn Pro His Leu Phe Asp Ile Leu
            290                 295                 300
```

-continued

```
Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
            325                 330                 335

Ile Thr Ser Pro Ile Tyr Gly Arg Glu Ala Asn Gln Glu Pro Pro Arg
                340                 345                 350

Ser Phe Thr Phe Asn Gly Pro Val Phe Arg Thr Leu Ser Xaa Pro Thr
        355                 360                 365

Leu Arg Leu Leu Gln Gln Pro Xaa Xaa Xaa Xaa Phe Asn Leu Arg
    370                 375                 380

Gly Xaa Glu Gly Val Glu Phe Ser Thr Pro Thr Asn Ser Phe Thr Tyr
385                 390                 395                 400

Arg Gly Arg Gly Xaa Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr Xaa Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
            565                 570                 575

Pro Phe Ser Phe Arg Ala Asn Pro Asp Ile Ile Gly Ile Ser Glu Gln
        580                 585                 590

Pro Leu Phe Gly Ala Gly Ser Ile Ser Ser Gly Glu Leu Tyr Ile Asp
    595                 600                 605

Lys Ile Glu Ile Ile Leu Ala Asp Ala Thr Phe Glu Ala Glu Ser Asp
610                 615                 620

Leu Glu Arg Ala Gln Lys Ala Val Asn Xaa Leu Phe Thr Ser Xaa Asn
625                 630                 635                 640

Gln Ile Gly Leu Lys Thr Asp Val Thr Asp Tyr His Ile Asp Gln Val
            645                 650                 655

Ser Asn Leu Val Glu Cys Leu Ser Asp Glu Phe Cys Leu Asp Glu Lys
        660                 665                 670

Xaa Glu Leu Ser Glu Lys Val Lys His Ala Xaa Xaa Leu Ser Asp Glu
    675                 680                 685

Arg Asn Leu Leu Gln Asp Pro Asn Phe Arg Gly Ile Asn Arg Gln Xaa
690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Xaa Gly Thr Phe Asp Glu
                725                 730                 735
```

-continued

```
Cys Tyr Xaa Thr Tyr Leu Tyr Gln Lys Ile Asp Glu Ser Lys Leu Lys
        740                 745                 750

Ala Tyr Thr Arg Tyr Xaa Leu Arg Gly Tyr Ile Glu Asp Ser Gln Asp
        755                 760                 765

Leu Glu Ile Tyr Leu Ile Arg Tyr Asn Ala Lys His Glu Thr Val Asn
        770                 775                 780

Val Pro Gly Thr Gly Ser Leu Trp Xaa Leu Ser Xaa Xaa Ser Ser Ile
785                 790                 795                 800

Gly Xaa Xaa Xaa Xaa Xaa Xaa Xaa Xaa Xaa Xaa Xaa Xaa Xaa Xaa Xaa
                805                 810                 815

Xaa Xaa Xaa Xaa Xaa Xaa Xaa Xaa Xaa Xaa Lys Cys Ala His His
        820                 825                 830

Ser His His Phe Ser Leu Asp Ile Asp Val Gly Cys Xaa Asp Leu Asn
        835                 840                 845

Glu Asp Leu Gly Val Trp Val Ile Phe Lys Ile Lys Thr Gln Asp Gly
        850                 855                 860

His Xaa Arg Leu Gly Xaa Leu Glu Phe Leu Glu Xaa Xaa Xaa Pro Leu
865                 870                 875                 880

Val Gly Glu Ala Leu Ala Arg Val Lys Arg Ala Glu Lys Lys Trp Arg
                885                 890                 895

Asp Lys Arg Glu Lys Leu Xaa Xaa Glu Thr Asn Ile Val Tyr Lys Glu
        900                 905                 910

Ala Lys Glu Ser Val Asp Ala Leu Phe Val Asn Ser Gln Tyr Asp Xaa
        915                 920                 925

Leu Gln Ala Asp Thr Asn Ile Ala Met Ile His Xaa Ala Asp Lys Arg
        930                 935                 940

Val His Xaa Ile Xaa Glu Ala Tyr Leu Pro Glu Leu Ser Val Ile Pro
945                 950                 955                 960

Gly Val Asn Ala Xaa Ile Phe Glu Glu Leu Gly Arg Ile Phe Thr
                965                 970                 975

Ala Phe Ser Leu Tyr Asp Ala Arg Asn Val Ile Lys Asn Gly Asp Phe
        980                 985                 990

Asn Asn Gly Leu Ser Cys Trp Asn Val Lys Gly His Val Asp Val Glu
        995                 1000                1005

Glu Gln Asn Asn Xaa Arg Ser Val Leu Val Val Pro Glu Trp Glu Ala
        1010                1015                1020

Glu Val Ser Gln Glu Val Arg Val Cys Pro Gly Arg Gly Tyr Ile Leu
1025                1030                1035                1040

Arg Val Thr Ala Tyr Lys Glu Gly Tyr Gly Xaa Gly Cys Val Thr Ile
                1045                1050                1055

His Glu Ile Glu Asn Asn Thr Asp Glu Leu Lys Phe Ser Asn Xaa Val
        1060                1065                1070

Glu Glu Glu Val Tyr Pro Asn Asn Thr Val Thr Cys Asn Asp Tyr Thr
        1075                1080                1085

Ala Xaa Gln Glu Glu Tyr Xaa Gly Xaa Tyr Thr Ser Xaa Asn Arg Gly
        1090                1095                1100

Tyr Asp Xaa Xaa Tyr Xaa Ser Asn Xaa Ser Val Pro Ala Asp Tyr Ala
1105                1110                1115                1120

Ser Xaa Tyr Glu Glu Lys Ala Tyr Thr Asp Gly Arg Arg Asp Asn Pro
        1125                1130                1135

Cys Glu Ser Asn Arg Gly Tyr Gly Asp Tyr Thr Pro Leu Pro Ala Gly
                1140                1145                1150

Tyr Val Thr Lys Xaa Leu Glu Tyr Phe Pro Glu Thr Asp Lys Val Trp
```

-continued

```
                1155                1160                1165
Ile Glu Ile Gly Glu Thr Glu Gly Thr Phe Ile Val Asp Ser Val Glu
    1170                1175                1180

Leu Leu Leu Met Glu Glu
1185                1190

(2) INFORMATION FOR SEQ ID NO:13:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Xaa Xaa Ile Asp Xaa Xaa Glu Xaa Xaa Xaa Xaa Xaa
1               5                   10
```